United States Patent
Louis

(10) Patent No.: US 12,036,391 B2
(45) Date of Patent: Jul. 16, 2024

(54) METHOD FOR DETERMINING AN UNCERTAINTY LEVEL OF DEEP REINFORCEMENT LEARNING NETWORK AND DEVICE IMPLEMENTING SUCH METHOD

(71) Applicant: DIABELOOP, Grenoble (FR)

(72) Inventor: Maxime Louis, Grenoble (FR)

(73) Assignee: DIABELOOP, Grenoble (FR)

( * ) Notice: Subject to any disclaimer, the term of this patent is extended or adjusted under 35 U.S.C. 154(b) by 0 days.

(21) Appl. No.: 18/511,672

(22) Filed: Nov. 16, 2023

(65) Prior Publication Data
US 2024/0165330 A1   May 23, 2024

(30) Foreign Application Priority Data
Nov. 23, 2022   (FR) ...................................... 2212200

(51) Int. Cl.
*G06N 20/00* (2019.01)
*A61M 5/172* (2006.01)
*G16H 20/17* (2018.01)

(52) U.S. Cl.
CPC ........... *A61M 5/1723* (2013.01); *G06N 20/00* (2019.01); *G16H 20/17* (2018.01)

(58) Field of Classification Search
CPC ...... G06N 20/00; G16H 20/17; A61M 5/1723
See application file for complete search history.

(56) References Cited

U.S. PATENT DOCUMENTS

| | | | |
|---|---|---|---|
| 2019/0214124 A1* | 7/2019 | Mougiakakou | G16H 50/20 |
| 2022/0039755 A1* | 2/2022 | Mikhno | A61B 5/7275 |
| 2023/0293099 A1* | 9/2023 | Kim | A61B 5/4821 |
| | | | 604/19 |

FOREIGN PATENT DOCUMENTS

CN   111048178 A   4/2020

OTHER PUBLICATIONS

Zhu, "An Insulin Bolus Advisor for Type 1 Diabetes Using Deep Reinforcement Learning", Sensors, 2020. (Year: 2020).*
Viroonluecha, "Evaluation of blood glucose level control in type 1 diabetic patients using deep reinforcement learning", PLOS One, Sep. 13, 2022. (Year: 2022).*
Ying Liu et al. "Deep Reinforcement Learning for Dynamic Treatment Regimes on Medical Registry Data", 2017 IEEE International Conference on Healthcare Informatics, Aug. 23, 2017, pp. 380-385.
Shamim Nemati et al. "Optimal Medication Dosing from Suboptimal Clinical Examples: A Deep Reinforcement Learning Approach", IEEE, Aug. 16, 2016, pp. 2978-2981.

(Continued)

*Primary Examiner* — Dave Misir

(57) ABSTRACT

Method for determining a recommendation value of a control parameter of a fluid infusion device. The method being implemented by a control device and comprising the steps of retrieving user data, feeding a deep reinforcement learning network, outputting a deep reinforcement learning network result, feeding an uncertainty certificates, outputting an uncertainty certificates result, comparing the uncertainty certificates result, determining the recommendation value, of a control parameter of the fluid infusion device based on a state of the unique user using a control algorithm or the deep reinforcement learning network.

10 Claims, 2 Drawing Sheets

(56) References Cited

OTHER PUBLICATIONS

Taiyu Zhu et al. "A Dual-Hormone Closed-Loop Delivery System for Type 1 Diabetes Using Deep Reinforcement Learning", Oct. 9, 2019, pp. 1-6.
Preliminary Search Report and Written Opinion dated Jul. 17, 2023 regarding French Application No. 2212200.

* cited by examiner

METHOD FOR DETERMINING AN UNCERTAINTY LEVEL OF DEEP REINFORCEMENT LEARNING NETWORK AND DEVICE IMPLEMENTING SUCH METHOD

FIELD OF THE INVENTION

The present invention relates to a method for determining an uncertainty level of deep reinforcement learning network and device implementing such method. More particularly, the present invention relates to a method for determining an uncertainty level of a deep reinforcement learning network used for determining a recommendation value of a control parameter of a fluid infusion device and a device implementing such method.

BACKGROUND OF THE INVENTION

In the field of healthcare, and more precisely in the field of treating diabetes, it is well known to determine a recommendation value corresponding to an insulin amount in order to maintain the blood glucose, also called glycemia, into a safe range, between hypoglycemia and hyperglycemia, called euglycemia.

Recently, so-called "closed-loop" systems were developed, where a processor is programmed to evaluate a volume rate of insulin to be injected, based on user-related data and/or time-based data, such as past and/or present glycemia measurements, and to control the injection of insulin based on this evaluation. In addition, the processor can be programmed to evaluate a volume of insulin to be injected in some special circumstances, in particular meals, and/or physical activity. The quantity can be injected to the user, subject to the user's approval. Such systems are also called "semi closed-loop" systems because of the necessary declaration by the patient of some of these special circumstances.

The time-based data is often used to predict the future glycemia. This prediction is then used to calculate the quantity of insulin having to be injected in order to maintain the glycemia in acceptable range.

An incorrect prediction of the future blood glucose can lead to an irrelevant calculated quantity of insulin to be injected, leading to a concentration of blood glucose in unacceptable intervals, where the patient may be in hypoglycemia and/or hyperglycemia.

One main drawback of this method is that the method can not precisely take into account all the parameters influencing the general behaviour of the glycemia. This leads to a determination of a recommendation value lacking accuracy.

The invention thus aims to answer at least partially the above presented technical problems and furthermore to address potential safety issues that a solution using reinforcement learning could bring.

BRIEF SUMMARY OF THE INVENTION

Thus, the invention relates to a method for determining a recommendation value of a control parameter of a fluid infusion device, the method being implemented by a control device and comprising the steps of:
retrieving user data, each data of the user data having a timestamp and the user data being related to a unique user, the user data comprising at least:
a plurality of amounts of a drug infused to the unique user;
a plurality of physiological values of the unique user;
a plurality of estimated values; and
wherein a plurality of amounts of a drug infused to the unique user, a physiological value of the unique user of the plurality of physiological values of the unique user and an estimated value of the plurality of estimated values represent a state of the unique user,
feeding a deep reinforcement learning network, such as the step of feeding a deep reinforcement learning network consists of giving a state of the unique user as an input to a deep reinforcement learning network, said deep reinforcement learning network comprising at least two layers;
outputting a deep reinforcement learning network result, such as the step of outputting the deep reinforcement learning network result consists of outputting a deep reinforcement learning network result for at least a penultimate layer of the at least two layers;
feeding uncertainty certificates, such as the step of feeding the uncertainty certificates consists of giving a result of the penultimate layer of the at least two layers as an input to said uncertainty certificates;
outputting an uncertainty certificate result, such as the step of outputting the uncertainty certificate result consists of outputting an uncertainty certificate result;
comparing the uncertainty certificate result, such as the step of comparing the uncertainty result consists of comparing the uncertainty result to an uncertainty threshold value, wherein the uncertainty threshold value represents a value under which the deep reinforcement learning network output is considered certain, otherwise, the deep reinforcement learning network output is considered uncertain; and if the deep reinforcement learning network is considered certain,
determining the recommendation value of a control parameter of the fluid infusion device based on a state of the unique user using the deep reinforcement learning network; else
determining the recommendation value of a control parameter of the fluid infusion device based on a state of the unique user using another control algorithm.

Such a configuration allows to estimate if an output of the deep reinforcement learning network is certain and accurate or, on the contrary, if said output is uncertain and inaccurate and therefore increase the safety of the method.

According to the present invention, a state of the unique user comprises a physiological value of the unique user of the plurality of physiological values of the unique user having a timestamp t, an estimated value of the plurality of estimated values having a timestamp sensibly equal to the timestamp t and a plurality of amounts of a drug infused to the unique user of the plurality of amounts of drug infused to the unique user having a timestamp sensibly equal or inferior to the timestamp t. According to the present invention, sensibly equal means equal plus or minus sixty seconds.

According to an embodiment, another control algorithm can be of any type such as a Proportional Derivative Integrative (PID) controller, or another deep reinforcement learning network algorithm for example.

According to an embodiment, the deep reinforcement learning network can be of any type such as a policy network, a deep neural network parametrization of Q-values (e.g. deep Q-learning, Actor critic . . . ) or a policy network trained to reproduce the behaviours induced by a Q-learning algorithm for example. In case the deep reinforcement learning network is a policy network, the output of said policy network corresponds to the recommendation value. In case the deep reinforcement learning network is a deep neural network parametrization of Q-values, the recommendation value is a value maximising the Q-value estimated by said deep neural network parametrization of Q-values.

According to an embodiment, the drug infused to the unique user corresponds to insulin infused to the unique user.

According to an embodiment, the recommendation value corresponds to a recommended value of insulin.

According to an embodiment, the plurality of physiological values of the unique user are blood glucose values.

According to an embodiment, the plurality of estimated values are Carbohydrates On Board (COB) values. A COB can be estimated based on blood glucose values and carbohydrates intakes such as meal size for example. A COB represents the carbohydrates ingested by the unique user whose impact cannot yet be measured in the blood glucose.

According to a specific embodiment compatible with the embodiments presented above, the user data also comprise at least one meal announcement. A state might then comprise a meal announcement.

According to the present invention, a meal announcement represents an announcement of a future meal at a future time having a certain amount of carbohydrates.

According to an embodiment, the policy network can be trained using any type of reinforcement learning algorithm such as policy gradient training algorithm, deterministic proximal policy gradient algorithm, actor-critic algorithm, or augmented random search algorithm for example.

According to an embodiment, the deep neural network parametrization of Q-values can be trained using Deep Q-learning, of Actor-critic algorithm for example.

According to an embodiment, the uncertainty certificates are optimised according to a loss function:

$$L(C)=1/n\Sigma i=1 \ldots b\ \Sigma j=1 \ldots n\ IC(Cj(\phi(xi)))+P(C)$$

where:

$I_C$ is any loss function applied to the outputs of each certificate;

P(C) is any penalty function on the certificates;

$\phi(x)$ is the output of the penultimate layer of the deep reinforcement learning network, of dimension d; and $(x_1, \ldots, x_n)$ represents a set of training states.

According to the present invention, the uncertainty certificates represent any set of functions $C_1, \ldots, C_n$ which are built to map any input close to the training set to 0 and map any input far from the training set to large values.

According to an embodiment, the uncertainty certificates comprise a set of functions of the state and wherein the functions of the state of the uncertainty certificates are functions which, to a state, associates its scalar product with a vector.

Such a configuration allows an easy training as functions which, to a state, associate its scalar product with a vector, do not have many parameters and can be computed efficiently. Such a configuration also allows to obtain a good accuracy as functions which, to a state, associates its scalar product with a vector are not susceptible to overfit and precisely generalise unseen states. It is also easier to implement an orthonormality constraint which guarantees a broad parametrization by certificates.

Such a configuration allows to obtain an accurate uncertainty certificate result and therefore improve the safety of the method while not needing an important computational load.

According to an embodiment, the functions of the state are trained so as to minimise a loss function:

$$L(C_1, \ldots, C_n)=1/n\ \Sigma_{i=1 \ldots n}\|C^T\phi(x_i)\|^2+\lambda\|C^TC-I_k\|$$

Where:

$\phi(x)$ is the output of the penultimate layer of the deep reinforcement learning network, of dimension d;

$(x_1, \ldots, x_n)$ represents a set of training states;

$(C_1, \ldots, C_k)$ represents the set of functions of the state, each having a dimension d+1;

$C^T$ represents a transpose of a matrix $C=(C_1, \ldots, C_k)$;

$(C^T\phi(x_i))_j$ is defined as $(C^T\phi(x_i))_j=\Sigma_{l=1 \ldots d}C_{lj}\phi(x_i)_l+C_{l,d+1}$;

$I_k$ represents an identity matrix of size k;

λ represents a parameter controlling the trade off between proximity of the certificates to the data and orthogonality of the certificates.

$\|C^T\phi(x_i)\|^2$ allows to motivate the certificates to map the $\phi(x)$ to 0, so that the certificates will parametrize the set of training states.

$\lambda\|\ C^TC-I_k\|$ allows to motivate the certificates to be orthogonal (which makes a parametrization of the set of functions of the state rich and identifiable).

Such a configuration allows to avoid determining the recommendation value of a control parameter of the fluid infusion device based on a state of the unique user using the deep reinforcement learning network when the state does not fit said deep reinforcement learning network as it has been found that the uncertainty increases as a glycemia noise and/or a meal announcement noise and/or an insulin infused noise increases.

According to an embodiment, $(C_1, \ldots, C_k)$ are initialised as random.

According to an embodiment, the uncertainty certificates comprise a set of functions of the state and wherein the functions of the state of the uncertainty certificates are neural networks.

Such a configuration allows to obtain a very accurate uncertainty certificate result and therefore improve the safety of the method.

According to an embodiment, the functions of the state are trained through simulations and the set of training states comprises specifically selected states, as the specifically selected states are selected based on the quality of the recommendation values determined by the deep reinforcement learning network based on said state.

Such a configuration allows to obtain a set of training states comprising specifically selected states such as the functions of the state are trained using states selected based on the quality of the recommendation values determined by the deep reinforcement learning network based on said state and therefore allows to obtain accurate uncertainty certificates.

According to an embodiment, the specifically selected states can be either simulated states or real states. A simulated state is a state obtained in a simulation environment while a real state is a state obtained by measuring and/or estimating values from a unique user. Using simulated states allows to increase the safety of the method as there is a straightforward way to identify states on which the deep reinforcement learning network would have performed well—just by evaluating the performances of the deep reinforcement learning network on the corresponding simulations.

According to an embodiment, the deep reinforcement learning network is a deep neural network. A deep neural network allows to obtain, most of the time, outputs having a great accuracy. Combined with a control algorithm used in case said outputs are uncertain, it allows to obtain an overall accurate and safe method.

According to an embodiment, the uncertainty threshold value is tuned after the training of functions of the state according to simulation results.

According to the present invention, simulation results are results of the method implemented in a simulation.

Such a configuration allows to increase the safety of the method as the uncertainty threshold is used to determine if the recommendation value will be determined by the deep reinforcement learning network or the control algorithm.

According to an embodiment, the uncertainty threshold is tuned so as to eliminate all states which lead to glycemia below 54 mg/dl and/or above to 250 mg/dL in the next hour. Such a configuration allows to greatly increase the safety of the method while maintaining a good efficiency.

According to an embodiment, the uncertainty threshold is tuned so as to maintain safety indicators such as a Time In Range (TIR) above a certain percentage X and/or an hypoglycemia time under a certain percentage Y and/or an hyperglycemia time under a certain percentage Z. The certain percentages X, Y and Z are reference method performances and can be modified according to the performances of the control algorithm in order to at least improve said control algorithm performances or greatly improve the safety of the method.

According to an embodiment, the uncertainty threshold value is obtained by running several simulations, each simulation having a different uncertainty threshold value and keeping the highest uncertainty threshold complying with the safety indicators.

The invention also relates to a method for determining an uncertainty of a deep reinforcement learning network output of an already trained deep reinforcement learning network comprising at least two layers, wherein the method is implemented by a control device and comprises the following steps:

retrieving input data, wherein the input data comprise at least a state, feeding the deep reinforcement learning network, such as the step of feeding the deep reinforcement learning network consists of giving the state as an input to the deep reinforcement learning network;

outputting a deep reinforcement learning network result, such as the step of outputting the deep reinforcement learning network result consists of outputting a deep reinforcement learning network result for at least a penultimate layer of the at least two layers;

feeding uncertainty certificates, such as the step of feeding the uncertainty certificates consists of giving a result of the penultimate layer of the at least two layers as an input to said uncertainty certificates;

outputting an uncertainty certificate result, such as the step of outputting the uncertainty certificate result consists of outputting an uncertainty certificate result;

comparing the uncertainty certificate result, such as the step of comparing the uncertainty result consists of comparing the uncertainty result to an uncertainty threshold value, wherein the uncertainty threshold value represents a value under which the deep reinforcement learning network output is considered certain;

wherein the uncertainty certificates comprises a set of functions of the state, said functions of the state are trained as follow:

$$L(C_1, \ldots, C_n) = 1/n \, \Sigma_{i=1 \ldots n} \|C^T \phi(x_i)\|^2 + \lambda \|C^T C - I_k\|$$

where:
$(x_1, \ldots, x_n)$ represents a set of training states;
$(C_1, \ldots, C_k)$ represents the set of functions of the state, each having a dimension d+1;
$C^T$ represents a transpose of a matrix $C=(C_1, \ldots, C_k)$;
$(C^T \phi(x_i))_k$ is defined as $(C^T \phi(x_i))_k = \Sigma_{k=1 \ldots d} C_{kl} \phi(x_i)_k + C_{d+1,k}$;
$I_k$ represents an identity matrix of size k;
$\lambda$ represents a parameter controlling the trade off between proximity of a plurality of certificates to the data and orthogonality of the certificates.

According to the present invention, the plurality of certificates represents a set of functions of $\phi(x)$.

Such a configuration allows to determine if an output of the deep reinforcement learning network is certain and accurate or, on the contrary, if said output is uncertain and inaccurate.

$\|C^T \phi(x_i)\|^2$ allows to motivate the certificates to map the $\phi(x)$ to 0, so that the certificates will parametrize the set of training states.

$\lambda \| C^T C - I_k\|$ allows to motivate the certificates to be orthogonal (which makes a parametrization of the set of functions of the state rich and identifiable).

According to the present invention, the deep reinforcement learning network output is the final output of the deep reinforcement learning network, the output of the last layer of the deep reinforcement learning network. In fact, except for the first layer, each layer of the at least two layers of the deep reinforcement learning network take as an input the deep reinforcement learning network result of the previous layer. In other words, according to an embodiment wherein there are more than two layers, the result of a first layer corresponds to the input of a second layer, and the result of the second layer corresponds to the result of the third layer, et cetera.

According to the present invention, the set of training states represents a set of states that are selected to be relevant for training purposes.

According to an embodiment, the states comprise meal announcements.

According to an embodiment, the training of the uncertainty certificates can be done as follow:

Inputs: a deep reinforcement learning network $\pi$, $\phi$: all but last layer of $\pi$. $(x_1, \ldots, x_n)$ a set of states. d: number of neurons in the last layer of $\pi$. Learning rate $\varepsilon$ (typically between 1e-3 and 1e-5 for example). Batch size b (typically between 1 and 32 for example).

Initialise the certificates $C=(C_1, \ldots, C_n)$ at random, each is of size/dimension (d+1).

For s in N

For each batch $(y_1, \ldots, y_b)$ of size b sampled from $(x_1, \ldots, x_n)$, using a stochastic gradient descent: iterate on data by batch Compute $L=1/n\Sigma i=1 \ldots b \|C^T\phi(yi)\|^2+\lambda\| C^T C-I_k\|$, as previously described Compute the gradient of L with respect to C: $\nabla C \, L$ Update $C=C-\varepsilon \nabla C \, L$ Outputs: The trained certificates $(C_1, \ldots, C_n)$.

According to an embodiment, the minimisation can be of any kind such as a stochastic gradient descent.

According to an embodiment, the learning rate $\varepsilon$ can be decreased exponentially from an initial value $\varepsilon_0$ down to a final value $\varepsilon_1$. This stimulates larger updates of the certificates during early steps of the training, and more precise steps towards the end. In other words, $\varepsilon$ can be decreased exponentially in order to "motivate" stronger changes in early iterations and smaller changes in later iterations. Such a configuration allows to avoid overshooting an optimum at each step.

The invention also relates to a computer program product comprising instructions which, when the program is executed by a computer, cause the computer to carry out the steps of the method as described above.

The invention also relates to a control device for determining a recommendation value of a control parameter of a fluid infusion device, the control device comprises:
- a retrieving unit, the retrieving unit being configured to retrieve user data, each data of the user data having a timestamp and the user data being related to a unique user, the user data comprising at least:
- a plurality of amounts of a drug infused to the unique user;
- a plurality of physiological values of the unique user; a plurality of estimated values;
- wherein a plurality of amounts of a drug infused to the unique user, a physiological value of the unique user of the plurality of physiological values of the unique user and an estimated value of the plurality of estimated values represent a state of the unique user,
- a recommendation unit, the recommendation unit being configured to determine the recommendation value based at least on a state of the unique user, wherein the recommendation unit is configured to determine the recommendation value by:
- feeding a deep reinforcement learning network, such as feeding a deep reinforcement learning network consists of giving a state of the unique user as an input to a deep reinforcement learning network, said deep reinforcement learning network comprising at least two layers;
- outputting a deep reinforcement learning network result, such as outputting the deep reinforcement learning network result consists of outputting a deep reinforcement learning network result for at least a penultimate layer of the at least two layers;
- feeding an uncertainty certificates, such as feeding the uncertainty certificates consists of giving a result of the penultimate layer of the at least two layers as an input to said uncertainty certificates;
- outputting an uncertainty certificate result, such as outputting the uncertainty certificate result consists of outputting an uncertainty certificate result;
- comparing the uncertainty certificate result, such as comparing the uncertainty result consists of comparing the uncertainty result to an uncertainty threshold value, wherein the uncertainty threshold value represents a value under which the deep reinforcement learning network output is considered certain, otherwise, the deep reinforcement learning network output is considered uncertain; and if the deep reinforcement learning network is considered certain,
- determining the recommendation value of a control parameter of the fluid infusion device based on a state of the unique user using the deep reinforcement learning network; else
- determining the recommendation value of a control parameter of the fluid infusion device based on a state of the unique user using a control algorithm.

According to an embodiment, the control device is configured to implement any of the embodiments of the methods described above such as the training of the uncertainty certificates for example.

The various non-incompatible aspects defined above can be combined.

BRIEF DESCRIPTION OF THE DRAWINGS

Embodiments of the invention will be described below with reference to the drawings, described briefly below.

DETAILED DESCRIPTION OF THE INVENTION

Figure 1:
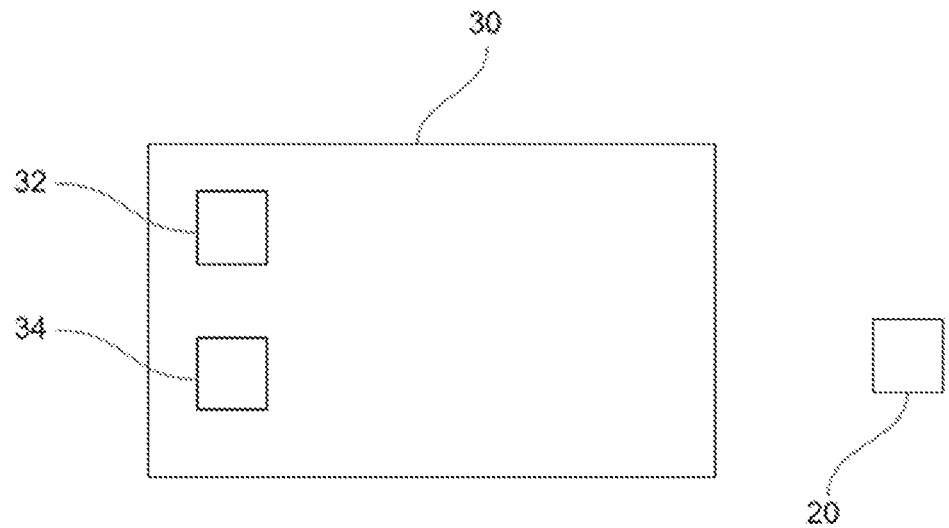
FIG. 1 shows a schematic view of a control device according to one embodiment of the invention.

As shown in FIG. 1, the present invention relates to a control device 30 for determining a recommendation value of a control parameter of a fluid infusion device 20, the control device 30 comprises:
- a retrieving unit 32, the retrieving unit 32 being configured to retrieve user data, each data of the user data having a timestamp and the user data being related to a unique user, the user data comprising at least:
- a plurality of amounts of a drug infused to the unique user;
- a plurality of physiological values of the unique user;
- a plurality of estimated values;
- wherein a plurality of amounts of a drug infused to the unique user, a physiological value of the unique user of the plurality of physiological values of the unique user and an estimated value of the plurality of estimated values represent a state of the unique user,
- a recommendation unit 34, the recommendation unit 34 being configured to determine the recommendation value based at least on a state of the unique user, wherein the recommendation unit 34 is configured to determine the recommendation value by:
- feeding a deep reinforcement learning network, such as feeding a deep reinforcement learning network consists of giving a state of the unique user as an input to a deep reinforcement learning network, said deep reinforcement learning network comprising at least two layers;
- outputting a deep reinforcement learning network result, such as outputting the deep reinforcement learning network result consists of outputting a deep reinforcement learning network result for at least a penultimate layer of the at least two layers;
- feeding uncertainty certificates, such as feeding the uncertainty certificates consists of giving a result of the penultimate layer of the at least two layers as an input to said uncertainty certificates;
- outputting an uncertainty certificate result, such as outputting the uncertainty certificate result consists of outputting an uncertainty certificate result;
- comparing the uncertainty certificate result, such as comparing the uncertainty result consists of comparing the uncertainty result to an uncertainty threshold value, wherein the uncertainty threshold value represents a value under which the deep reinforcement learning network output is considered certain, otherwise, the deep reinforcement learning network output is considered uncertain; and if the deep reinforcement learning network is considered certain, determining the recommendation value of a control parameter of the fluid infusion device 20 based on a state of the unique user using the deep reinforcement learning network; else determining the recommendation value of a control parameter of the fluid infusion device 20 based on a state of the unique user using a control algorithm.

According to an embodiment, the control device 30 is configured to implement any of the embodiments of methods described below.

Figure 2:
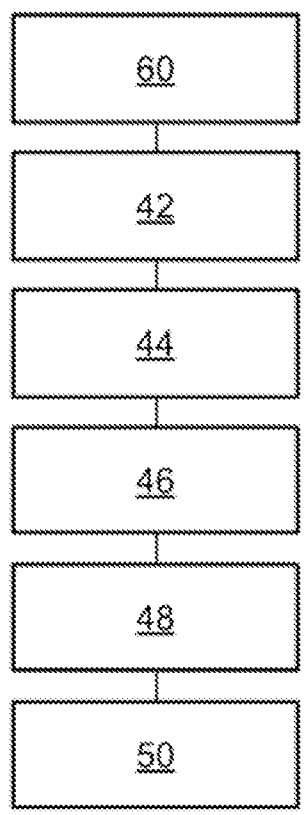
FIG. 2 shows steps of a method for determining an uncertainty of a deep reinforcement learning network output of an already trained deep reinforcement learning network according to one embodiment of the invention.

As shown in FIG. 2, the present invention also relates to a method for determining an uncertainty of a deep reinforcement learning network output of an already trained deep reinforcement learning network comprising at least two layers, wherein the method is implemented by a control device 30 and comprises the following steps:

retrieving input data 60, wherein the input data comprise at least a state, feeding the deep reinforcement learning network 42, such as the step of feeding the deep reinforcement learning network 42 consists of giving the state as an input to the deep reinforcement learning network;

outputting a deep reinforcement learning network result 44, such as the step of outputting the deep reinforcement learning network result 44 consists of outputting a deep reinforcement learning network result for at least a penultimate layer of the at least two layers;

feeding uncertainty certificates 46, such as the step of feeding the uncertainty certificates 46 consists of giving a result of the penultimate layer of the at least two layers as an input to said uncertainty certificates;

outputting an uncertainty certificate result 48, such as the step of outputting the uncertainty certificate result 48 consists of outputting an uncertainty certificate result;

comparing the uncertainty certificate result 50, such as the step of comparing the uncertainty result 50 consists of comparing the uncertainty result to an uncertainty threshold value, wherein the uncertainty threshold value represents a value under which the deep reinforcement learning network output is considered certain;

wherein the uncertainty certificates comprises a set of functions of the state, said functions of the state are trained as follow:

$$L(C_1, \ldots, C_k) = \frac{1}{n}\sum_{i=1\ldots n}\|C^T\phi(x_i)\|^2 + \lambda\|C^TC - I_k\|$$

where:

$(x_1, \ldots, x_n)$ represents a set of training states;

$(C_1, \ldots, C_k)$ represents the set of functions of the state, each having a dimension d+1;

$C^T$ represents a transpose of a matrix $C=(C_1, \ldots, C_k)$;

$(C^T\phi(x_i))_j$ is defined as $(C^T\phi(x_i))_j = \Sigma_{l=1\ldots d} C_{l,j}\phi(x_i)_l + C_{l,d+1}$;

$I_k$ represents an identity matrix of size k;

$\lambda$ represents a parameter controlling the trade off between proximity of a plurality of certificates to the data and orthogonality of the certificates; and the plurality of certificates represents a set of functions of $\phi(x)$.

Such a configuration allows to determine if an output of the deep reinforcement learning network is certain and accurate or, on the contrary, if said output is uncertain and inaccurate. $\|C^T\phi(x_i)\|^2$ allows to motivate the certificates to map the $\phi(x)$ to 0, so that the certificates will parametrize the set of training states. $\lambda\|C^TC - I_k\|$ allows to motivate the certificates to be orthogonal (which makes a parametrization of the set of functions of the state rich and identifiable).

According to the present invention, the deep reinforcement learning network output is the final output of the deep reinforcement learning network, the output of the last layer of the deep reinforcement learning network. In fact, except for the first layer, each layer of the at least two layers of the deep reinforcement learning network take as an input the deep reinforcement learning network result of the previous layer. In other words, according to an embodiment wherein there are more than two layers, the result of a first layer corresponds to the input of a second layer, and the result of the second layer corresponds to the result of the third layer, et cetera.

The set of training states represents a set of states that are selected to be relevant for training purposes. Such a characteristic allows to efficiently train the set of functions of the state.

According to an embodiment, the training of the uncertainty certificates can be done as follow:

Inputs: a deep reinforcement learning network $\pi$, $\phi$: all but last layer of $\pi$. $(x_1, \ldots, x_n)$ a set of states. d: number of neurons in the last layer of $\pi$. Learning rate $\varepsilon$ (typically between 1e-3 and 1e-5 for example). Batch size b (typically between 1 and 32 for example).

Initialise the certificates $C=(C_1, \ldots, C_n)$ at random, each is of size/dimension (d+1).

For s in N

For each batch $(y_1, \ldots, y_b)$ of size b sampled from $(x_1, \ldots, x_n)$, using a stochasticgradient descent: iterate on data by batch Compute $L = 1/n\Sigma i=1 \ldots b\|CT\phi(yi)\|2 + \lambda\|$ CT C−Ik$\|$, as previously described Compute the gradient of L with respect to C: $\nabla C\ L$ Update $C = C - \varepsilon\nabla C\ L$ Outputs: The trained certificates $(C_1, \ldots, C_n)$.

According to an embodiment, the minimisation can be of any kind such as a stochastic gradient descent.

According to an embodiment, the learning rate $\varepsilon$ can be decreased exponentially from an initial value $\varepsilon_0$ down to a final value $\varepsilon_1$. This stimulates larger updates of the certificates during early steps of the training, and more precise steps towards the end. In other words, $\varepsilon$ can be decreased exponentially in order to "motivate" stronger changes in early iterations and smaller changes in later iterations. Such a configuration allows to avoid overshooting an optimum at each step.

Figure 3:
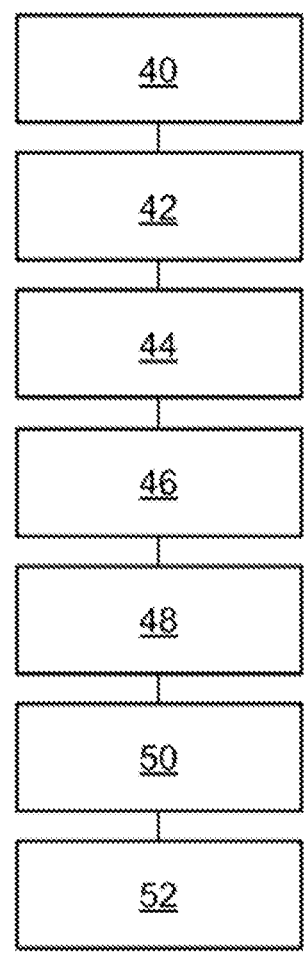
FIG. 3 shows steps of a method for determining the recommendation value of a control parameter of the fluid infusion device according to one embodiment of the invention.

As shown in FIG. 3, the present invention also relates to a method for determining a recommendation value of a control parameter of a fluid infusion device 20. The method implemented by the control device 30 described above and comprises a step of retrieving user data 40. Each data of the user data has a timestamp and the user data is related to a unique user. The user data comprises a plurality of amounts of a drug infused to the unique user, a plurality of physiological values of the unique user, and a plurality of estimated values. A plurality of amounts of a drug infused to the unique user, a physiological value of the unique user of the plurality of physiological values of the unique user and an estimated value of the plurality of estimated values represent a state of the unique user. The drug infused to the unique user corresponds to insulin infused to the unique user and the plurality of physiological values of the unique user are blood glucose values. The plurality of estimated values are Carbohydrates On Board (COB) values. A COB can be estimated based on blood glucose values and carbohydrates intakes such as meal size for example. A COB represents the carbohydrates ingested by the unique user whose impact cannot yet be measured in the blood glucose. Therefore, the user data also comprise at least one meal announcement. A state then comprises a meal announcement representing an announcement of a future meal at a future time having a certain amount of carbohydrates.

According to the present invention, a state of the unique user comprises a physiological value of the unique user of the plurality of physiological values of the unique user having a timestamp t, an estimated value of the plurality of estimated values having a timestamp sensibly equal to the timestamp t and a plurality of amounts of a drug infused to the unique user of the plurality of amounts of drug infused to the unique user having a timestamp sensibly equal or inferior to the timestamp t. According to the present invention, sensibly equal means equal plus or minus sixty seconds.

The method comprises a step of feeding a deep reinforcement learning network 42. The step of feeding a deep reinforcement learning network 42 consists of giving a state of the unique user as an input to a deep reinforcement learning network, said deep reinforcement learning network comprises at least two layers.

The method also comprises a step of outputting a deep reinforcement learning network result 44. The step of outputting the deep reinforcement learning network result 44 consists of outputting a deep reinforcement learning network result for at least a penultimate layer of the at least two layers.

The method also comprises a step of feeding uncertainty certificates 46. The step of feeding the uncertainty certificates 46 consists of giving a result of the penultimate layer of the at least two layers as an input to said uncertainty certificates.

The method also comprises a step of outputting an uncertainty certificate result 48. The step of outputting the uncertainty certificate result 48 consists of outputting an uncertainty certificate result.

The method also comprises a step of comparing the uncertainty certificate result 50. The step of comparing the uncertainty result 50 consists of comparing the uncertainty result to an uncertainty threshold value. The uncertainty threshold value represents a value under which the deep reinforcement learning network output is considered certain, otherwise, the deep reinforcement learning network output is considered uncertain.

If the deep reinforcement learning network is considered certain, the method comprises a step of determining the recommendation value 52 of a control parameter of the fluid infusion device 20 based on a state of the unique user using the deep reinforcement learning network. The deep reinforcement learning network can be of any type such as a policy network, a deep neural network parametrization of Q-values (e.g. deep Q-learning, Actor critic . . . ) or a policy network trained to reproduce the behaviours induced by a Q-learning algorithm for example. In case the deep reinforcement learning network is a policy network, the output of said policy network corresponds to the recommendation value. In case the deep reinforcement learning network is a deep neural network parametrization of Q-values, the recommendation value is a value maximising the Q-value estimated by said deep neural network parametrization of Q-values. The policy network can be trained using any type of reinforcement learning algorithm such as policy gradient training algorithm, deterministic proximal policy gradient algorithm, actor-critic algorithm, or augmented random search algorithm for example. The Q-learning algorithm can be trained using Deep Q-learning, of Actor-critic algorithm for example.

If the deep reinforcement learning network is considered uncertain, the method comprises a step of determining the recommendation value 52 of a control parameter of the fluid infusion device 20 based on a state of the unique user using another control algorithm. Another control algorithm can be of any type such as a Proportional Derivative Integrative (PID) controller, or another deep reinforcement learning network algorithm for example.

Such characteristics allow to estimate if an output of the deep reinforcement learning network is certain and accurate or, on the contrary, if said output is uncertain and inaccurate and therefore increase the safety of the method. The output corresponding to the result of the last layer of the deep reinforcement learning network.

The uncertainty certificates are optimised according to a loss function:

$$L(C)=1/n\Sigma i=1 \ldots b\ \Sigma j=1 \ldots n\ IC(Cj(\phi(xi)))+P(C)$$

where:

$I_C$ is any loss function applied to the outputs of each certificate;

P(C) is any penalty function on the certificates;

$\phi(x)$ is the output of the penultimate layer of the deep reinforcement learning network, of dimension d; and $(x_1, \ldots, x_n)$ represents a set of training states.

The uncertainty certificates represent any set of functions $C_1, \ldots, C_n$ which are built to map any input close to the training set to 0 and map any input far from the training set to large values.

According to a specific embodiment, the uncertainty certificates comprise a set of functions of the state and wherein the functions of the state of the uncertainty certificates are functions which, to a state, associates its scalar product with a vector. Such a configuration allows an easy training as functions which, to a state, associate its scalar product with a vector, do not have many parameters and can be computed efficiently. Such a configuration also allows to obtain a good accuracy as functions which, to a state, associates its scalar product with a vector are not susceptible to overfit and precisely generalise unseen states. It is also easier to implement an orthonormality constraint which guarantees a broad parametrization by certificates. Such a configuration also allows to obtain an accurate uncertainty certificate result and therefore improve the safety of the method while not needing an important computational load. In this specific embodiment, the functions of the state are trained so as to minimise a loss function:

$$L(C_1, \ldots, C_k) = \frac{1}{n}\sum\nolimits_{i=1\ldots n}\|C^T\phi(x_i)\|^2 + \lambda\|C^TC-I_k\|$$

where:

$(x_1, \ldots, x_n)$ represents a set of training states;

$(C_1, \ldots, C_k)$ represents the set of functions of the state, each having a dimension d+1;

CT represents a transpose of a matrix $C=(C_1, \ldots, C_k)$;

$(C^T\phi(x_i))_j$ is defined as $(C^T\phi(x_i))_j=\Sigma_{l=1 \ldots d}C_{lj}\phi(x_i)_l + C_{l,d+1}$;

$I_k$ represents an identity matrix of size k;

λ represents a parameter controlling the trade off between proximity of a plurality of certificates to the data and orthogonality of the certificates; and the plurality of certificates represents a set of functions of φ(x).

$(C_1, \ldots, C_k)$ represents the set of functions of the state initialised as random, each having a dimension d+1;

$\|C^T\phi(x_i)\|^2$ allows to motivate the certificates to map the φ(x) to 0, so that the certificates will parametrize the set of training states. $\lambda\|C^TC-I_k\|$ allows to motivate the certificates to be orthogonal (which makes a parametrization of the set of functions of the state rich and identifiable). Such a configuration also allows to avoid determining the recommendation value of a control parameter of the fluid infusion device 20 based on a state of the unique user using the deep reinforcement learning network when the state does not fit said deep reinforcement learning network as it has been found that the uncertainty increases as a glycemia noise and/or a meal announcement noise and/or an insulin infused noise increases.

According to an embodiment, the functions of the state of the uncertainty certificates are neural networks. Such a configuration allows to obtain a very accurate uncertainty certificate result and therefore improve the safety of the method.

The functions of the state are trained through simulations and the set of training states comprises specifically selected states, as the specifically selected states are selected based on the quality of the recommendation values determined by the deep reinforcement learning network based on said state. Such a configuration allows to obtain a set of training states comprising specifically selected states such as the functions of the state are trained using states selected based on the quality of the recommendation values determined by the deep reinforcement learning network based on said state and therefore allows to obtain accurate uncertainty certificates. The specifically selected states are simulated states. A simulated state is a state obtained in a simulation environment while a real state is a state obtained by measuring and/or estimating values from a unique user. Using simulated states allows to increase the safety of the method as there is a straightforward way to identify states on which the deep reinforcement learning network would have performed well—just by evaluating the performances of the deep reinforcement learning network on the corresponding simulations.

According to an embodiment, the deep reinforcement learning network is a deep neural network. A deep neural network allows to obtain, most of the time, outputs having a great accuracy. Combined with a control algorithm used in case said outputs are uncertain, it allows to obtain an overall accurate and safe method.

The uncertainty threshold value is tuned after the training of functions of the state according to simulation results. According to the present invention, simulation results are results of the method implemented in a simulation. Such a configuration allows to increase the safety of the method as the uncertainty threshold is used to determine if the recommendation value will be determined by the deep reinforcement learning network or the control algorithm. The uncertainty threshold is tuned so as to eliminate all states which lead to glycemia below 54 mg/dl and/or above to 250 mg/dL in the next hour. Such a configuration allows to greatly increase the safety of the method while maintaining a good efficiency. Indeed 54 mg/dl and 250 mg/dL allows to obtain a good balance between safety and efficiency as 54 mg/dl and 250 mg/dL while being extreme blood glucose values and have to be avoided are still relatively acceptable for a short period of time, depending on the unique user. The uncertainty threshold is tuned so as to maintain safety indicators such as a Time In Range (TIR) above a certain percentage X and/or an hypoglycemia time under a certain percentage Y and/or an hyperglycemia time under a certain percentage Z. The certain percentages X, Y and Z are reference method performances and can be modified according to the performances of the control algorithm in order to at least improve said control algorithm performances or greatly improve the safety of the method. The uncertainty threshold value is obtained by running several simulations, each simulation having a different uncertainty threshold value and keeping the highest threshold complying with the safety indicators.

The invention also relates to a computer program product comprising instructions which, when the program is executed by a computer, cause the computer to carry out the steps of the method described above.

While exemplary embodiments of the invention have been described, it will be understood by those skilled in the art that various changes, omissions and/or additions may be made, and equivalents may be substituted for elements thereof without departing from the spirit and scope of the invention. In addition, many modifications may be made to adapt a particular situation or material to the teachings of the invention without departing from the scope thereof. Therefore, it is intended that the invention is not limited to the particular embodiments disclosed for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

While exemplary embodiment of the invention has been described with reference to two main embodiments, it will be understood by those skilled in the art that various changes, omissions and/or additions may be made, and equivalents may be substituted for elements thereof without departing from the spirit and scope of the invention. In addition, many modifications may be made to adapt a particular situation or material to the teachings of the invention without departing from the scope thereof. Therefore, it is intended that the invention is not limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

The invention claimed is:

1. A method for determining a recommendation value of a control parameter of a fluid infusion device, the method being implemented by a control device and comprising:
   retrieving user data, each data of the user data having a timestamp and the user data being related to a unique user, the user data comprising at least:
   a plurality of amounts of a drug infused to the unique user;
   a plurality of physiological values of the unique user;
   a plurality of estimated values; and
   wherein a plurality of amounts of a drug infused to the unique user, a physiological value of the unique user of the plurality of physiological values of the unique user and an estimated value of the plurality of estimated values represent a state of the unique user, feeding a deep reinforcement learning network, wherein the step of feeding the deep reinforcement learning network consists of giving the state of the unique user as an input to the deep reinforcement learning network, the deep reinforcement learning network comprising at least two layers;

outputting a deep reinforcement learning network result, wherein the step of outputting the deep reinforcement learning network result consists of outputting the deep reinforcement learning network result for at least a penultimate layer of the at least two layers;

feeding uncertainty certificates, wherein the step of feeding the uncertainty certificates consists of giving a result of the penultimate layer of the at least two layers as an input to the uncertainty certificates;

outputting an uncertainty certificate result, wherein the step of outputting the uncertainty certificate result consists of outputting the uncertainty certificate result;

comparing the uncertainty certificate result, wherein the step of comparing the uncertainty certificate result consists of comparing the uncertainty certificate result to an uncertainty threshold value, wherein the uncertainty threshold value represents a value under which the deep reinforcement learning network output is considered certain, otherwise, the deep reinforcement learning network output is considered uncertain; and if the deep reinforcement learning network is considered certain, determining the recommendation value of the control parameter of the fluid infusion device based on the state of the unique user using the deep reinforcement learning network; else determining the recommendation value of the control parameter of the fluid infusion device based on the state of the unique user using another control algorithm.

2. The method for determining a recommendation value of a control parameter of a fluid infusion device according to claim 1, wherein the uncertainty certificates are optimised according to a loss function:

$$L(C)=1/n\Sigma i=1 \ldots b\ \Sigma j=1 \ldots n\ IC(Cj(\phi(xi)))+P(C)$$

where:
lc is any loss function applied to the outputs of each certificate;
P(C) is any penalty function on the certificates;
$\phi(x)$ is the output of the penultimate layer of the deep reinforcement learning network, of dimension d; and
$(x_1, \ldots, x_n)$ represents a set of training states.

3. The method for determining a recommendation value of a control parameter of a fluid infusion device according to claim 1, wherein the uncertainty certificates comprise a set of functions of the state of the unique user and wherein the functions of the state of the unique user of the uncertainty certificates are functions which, to a state, associates its scalar product with a vector.

4. The method for determining a recommendation value of a control parameter of a fluid infusion device according to claim 3, wherein the functions of the state are trained so as to minimise a loss function:

$$L(C_1, \ldots, C_n)=1/n\ \Sigma_{i=1 \ldots n}\|C^T\phi(x_i)\|^2+\lambda\|C^TC-I_k\|$$

Where:
$\phi(x)$ is the output of the penultimate layer of the deep reinforcement learning network, of dimension d;
$(x_1, \ldots, x_n)$ represents a set of training states;
$(C_1, \ldots, C_k)$ represents the set of functions of the state, each having a dimension d+1;
$C^T$ represents a transpose of a matrix $C=(C_1, \ldots, C_k)$;
$(C^T\phi(x_i))_j$ is defined as $(C^T\phi(x_i))_j=\Sigma_{l=1 \ldots d}C_{lj}\phi(x_i)_l+C_{l,d+1}$;
$I_k$ represents an identity matrix of size k;
$\lambda$ represents a parameter controlling the trade off between proximity of the certificates to the data and orthogonality of the certificates.

5. The method for determining a recommendation value of a control parameter of a fluid infusion device according to claim 1, wherein the uncertainty certificates comprise a set of functions of the state of the unique user and wherein the functions of the state of the unique user of the uncertainty certificates are neural networks.

6. The method for determining a recommendation value of a control parameter of a fluid infusion device according to claim 3, wherein the functions of the state are trained through simulations and a set of training states comprises specifically selected states, as the specifically selected states are selected based on a quality of the recommendation values determined by the deep reinforcement learning network based on said state.

7. The method for determining a recommendation value of a control parameter of a fluid infusion device according to claim 1, wherein the uncertainty threshold value is tuned after a training of functions of the state according to simulation results.

8. A non-transitory computer program product comprising instructions which, when executed by a computer, cause the computer to carry out the steps of the method of claim 1.

9. A method for determining an uncertainty of a deep reinforcement learning network output of an already trained deep reinforcement learning network comprising at least two layers, wherein the method is used to determine a recommendation value of a control parameter for a device, is implemented by a control device, and comprises:

retrieving input data, wherein the input data comprise at least a state related to a process controlled by the device, feeding the deep reinforcement learning network, wherein the step of feeding the deep reinforcement learning network consists of giving the state as an input to the deep reinforcement learning network;

outputting the deep reinforcement learning network result, wherein the step of outputting the deep reinforcement learning network result consists of outputting the deep reinforcement learning network result for at least a penultimate layer of the at least two layers;

feeding uncertainty certificates, wherein the step of feeding the uncertainty certificates consists of giving a result of the penultimate layer of the at least two layers as an input to the uncertainty certificates;

outputting an uncertainty certificate result, wherein the step of outputting the uncertainty certificate result consists of outputting the uncertainty certificate result;

comparing the uncertainty certificate result, wherein the step of comparing the uncertainty certificate result consists of comparing the uncertainty certificate result to an uncertainty threshold value, wherein the uncertainty threshold value represents a value under which the deep reinforcement learning network output is considered certain;

determining the recommendation value based on the state using the deep reinforcement learning network when comparing the uncertainty certificate indicates that the deep reinforcement learning network output is considered certain; and determining the recommendation value based on the state using another control algorithm when comparing the uncertainty certificate indicates that the deep reinforcement learning network output is not considered certain, wherein the uncertainty certificates comprises a set of functions of the state, said functions of the state are trained as follow:

$$L(C_1,\ldots,C_n)=1/n\, \Sigma_{i=1\ldots n}\|C^T\phi(x_i)\|^2+\lambda\|C^TC-I_k\|$$

where:

($x_1, \ldots, x_n$) represents a set of training states;

($C_1, \ldots, C_k$) represents the set of functions of the state, each having a dimension d+1;

$C^T$ represents a transpose of a matrix $C=(C_1, I, C_k)$;

$C^T\phi(x_i))_k$ is defined as $(C^T\phi(x_i))_k = \Sigma_{k=1\ldots d} C_{ki}\phi(x_i)_k + C_{d+1,k}$;

$I_k$ represents an identity matrix of size k;

$\lambda$ represents a parameter controlling the trade off between proximity of a plurality of certificates to the data and orthogonality of the certificates.

10. A control device for determining a recommendation value of a control parameter of a fluid infusion device, the control device comprises:
a retrieving unit, the retrieving unit being configured to retrieve user data, each data of the user data having a timestamp and the user data being related to a unique user, the user data comprising at least:
a plurality of amounts of a drug infused to the unique user;
a plurality of physiological values of the unique user;
a plurality of estimated values;
wherein a plurality of amounts of a drug infused to the unique user, a physiological value of the unique user of the plurality of physiological values of the unique user and an estimated value of the plurality of estimated values represent a state of the unique user,
a recommendation unit, the recommendation unit being configured to determine the recommendation value based at least on the state of the unique user, wherein the recommendation unit is configured to determine the recommendation value by:
feeding a deep reinforcement learning network, wherein feeding the deep reinforcement learning network consists of giving the state of the unique user as an input to the deep reinforcement learning network, the deep reinforcement learning network comprising at least two layers;
outputting a deep reinforcement learning network result, wherein outputting the deep reinforcement learning network result consists of outputting the deep reinforcement learning network result for at least a penultimate layer of the at least two layers;
feeding an uncertainty certificates, such as wherein feeding the uncertainty certificates consists of giving a result of the penultimate layer of the at least two layers as an input to the uncertainty certificates;
outputting an uncertainty certificate result, wherein outputting the uncertainty certificate result consists of outputting an uncertainty certificate result;
comparing the uncertainty certificate result, wherein comparing the uncertainty certificate result consists of comparing the uncertainty certificate result to an uncertainty threshold value, wherein the uncertainty threshold value represents a value under which the deep reinforcement learning network output is considered certain, otherwise, the deep reinforcement learning network output is considered uncertain; and if the deep reinforcement learning network is considered certain,
determining the recommendation value of the control parameter of the fluid infusion device based on the state of the unique user using the deep reinforcement learning network; else
determining the recommendation value of the control parameter of the fluid infusion device based on the state of the unique user using a control algorithm.

* * * * *